United States Patent [19]
Saisaka et al.

[11] Patent Number: 5,624,424
[45] Date of Patent: Apr. 29, 1997

[54] DISPOSABLE DIAPER

[75] Inventors: Miyuki Saisaka, Tokyo; Masaru Tsubata, Soka; Yoshio Hirai, Tokyo; Mie Takahashi, Kasugai; Sadayoshi Terada, Kamakura, all of Japan

[73] Assignee: New OJI Paper Co., Ltd., Tokyo, Japan

[21] Appl. No.: 391,649

[22] Filed: Feb. 21, 1995

[30] Foreign Application Priority Data

| Feb. 25, 1994 | [JP] | Japan | 6-051042 |
| Nov. 11, 1994 | [JP] | Japan | 6-301694 |
| Jan. 6, 1995 | [JP] | Japan | 7-015600 |

[51] Int. Cl.⁶ ............................. A61F 13/15
[52] U.S. Cl. ....................... 604/385.2; 604/385.1
[58] Field of Search .............. 604/385.1, 385.2, 604/367, 358.378

[56] References Cited

U.S. PATENT DOCUMENTS

| 4,704,116 | 11/1987 | Enloe | 604/385 |
| 4,846,825 | 7/1989 | Enloe et al. | 604/385.1 |
| 4,940,464 | 7/1990 | Gompel et al. | 604/396 |
| 5,374,259 | 12/1994 | Takahashi et al. | 604/367 |

FOREIGN PATENT DOCUMENTS

| 0623331 | 9/1994 | European Pat. Off. . |
| 3-80859 | 4/1991 | Japan . |
| 3-162854 | 7/1991 | Japan . |
| 4-161152 | 6/1992 | Japan . |
| 5-76565 | 3/1993 | Japan . |
| 6-63074 | 3/1994 | Japan . |

*Primary Examiner*—Mary Beth Jones
*Assistant Examiner*—David J. Cho
*Attorney, Agent, or Firm*—Armstrong, Westerman, Hattori, McLeland & Naughton

[57] ABSTRACT

A disposable diaper having an excellent fit to the wearer has an outer member (2) having front and back waist sections (4, 5) and crotch sections (6), and a liquid absorbent member (3), wherein the outer member includes an outermost sheet layer (21) and a pair of side liner sheet layers (22), and the liquid absorbent member includes a liquid non-permeable back sheet layer (13), a liquid permeable top sheet layer (14) and a liquid absorbent pad layer (15) interposed between the back and top sheet layers, each side liner sheet layer being formed from a composite sheet including an elastic sheet ply capable of expansion and contraction in the transversal direction of the diaper and at least one non-elastic sheet ply laminated on at least one surface of the elastic sheet ply and capable of elongation in the transversal direction of the diaper.

12 Claims, 9 Drawing Sheets

DISPOSABLE DIAPER

BACKGROUND OF THE INVENTION

1. Field of the Invention

The present invention relates to a disposable diaper. More particularly, the present invention relates to a disposable diaper having a satisfactory expansion and contraction property and a fiber-fabric-like skin feeling, where at least the side liner portions of which diaper are formed from a specific stretchable, moisture-permeable composite sheet.

The disposable diaper of the present invention is useful for babies and incontinent persons.

2. Description of the Related Art

Japanese Unexamined Patent Publication (Kokai) No. 3-80,859 discloses a disposable undershirt in which a sheet prepared by segmentally or separately adhering a stretchable film to an inside surface of a stretchable nonwoven fabric is employed as a back sheet. Also, Japanese Unexamined Patent Publication (Kokai) No. 3-162,854 discloses a disposable garment in which a stretchable film is segmentally or separately attached to an inside surface of a stretchable nonwoven fabric to form a sheet, and a plurality of air-permeable holes are formed on both side edge portions of the stretchable film on the sheet.

The disposable diaper includes an underpants type disposable diaper in which the front waist section and the back waist section of the diaper are adhered and fixed to each other at side edge portions thereof so as to form a waist opening and a pair of crotch openings. The underpants type disposable diaper can be put on and taken off by the wearer himself and thus is useful for diaper-wearing children and incontinent adults. Recently, the demand for underpants type disposable diapers has been increasing.

For the underpants type disposable diaper, it is required that the crotch opening portions, waist opening portions and waist side portions are appropriately fit to the wearer. Therefore, the above-mentioned portions are formed from a stretchable elastic material.

Japanese Unexamined Patent Publication No. 2-4364 discloses an underpants type disposable diaper having a liquid-absorbent pad member formed from a liquid-permeable top sheet, a liquid non-permeable back sheet and a liquid absorbent pad arranged between the top and back sheet, and a pair of stretchable side panels attached to side edge portions of the liquid absorbent pad member.

This type of diaper has a satisfactory leak-preventing property at the waist and crotch opening portions. However, this diaper is disadvantageous in that $a_0$ the waist portions exhibits an unsatisfactory fit to the wearer; $b_0$ when the stretchable side panels are attached to the liquid absorbent pad member, since the middle portions of the side panels are attached in a stretched condition to the crotch portions of the liquid absorbent pad member, and the remaining portions of the side panel are in a non-stretched condition, it is difficult to fix the stretchable side panels in the stretched condition at predetermined intervals in a direction in which the diaper-production line moves; $c_0$ the stretchable side panels are not strong enough to fit the diaper to the wearer; and $d_0$ since the crotch opening portions have no gathers, the diaper is unsatisfactory in preventing the liquid from leaking through the crotch openings.

Also, another underpants type disposable diaper comprising an absorbent pad member formed from a top sheet, a back sheet and an absorbent pad arranged between the above-mentioned sheets, and an outermost sheet member for fixing the absorbent pad member thereon and holding the diaper on the wearer by bringing the outermost sheet member into contact with the wearer, is disclosed in Unexamined PCT Publication (Kokai) No. 1-503,473 in Japan, Japanese Unexamined Patent Publication (Kokai) No. 4-161,152, Japanese Unexamined Patent Publication (Kokai) No. 5-76,565 or Japanese Unexamined Patent Publication (Kokai) No. 6-63,074.

The disposable diaper disclosed in Japanese Unexamined Patent Publication (Kokai) No. 3-80,859 and Japanese Unexamined Patent Publication (Kokai) No. 3-162,854, in which a diaper consists of a sheet prepared by segmentally adhering a stretchable film to an inside surface of a stretchable nonwoven fabric is employed as a back sheet, is disadvantageous in that the stretchable nonwoven fabric is more expensive not only in the raw material thereof but also in the cost of the production process thereof, compared to conventional non-stretchable materials, thereby increasing the cost to general consumers.

Also, where the stretchable composite sheet is employed as a back sheet, this sheet is required to serve as a leakage-preventing sheet, and thus must be non-permeable to liquids. The liquid non-permeable sheet causes the wearer of the resultant diaper to feel stuffy due to the body heat of the wearer or when the ambient temperature increases. To prevent the stuffiness, a plurality of ventilating holes are formed in portions of the side flaps on the back sheet except for the crotch portions of the flaps. These ventilating holes cause the disadvantage that if the wearer of the diaper, who is lying down, especially sleeping, excretes, the excrement can leak through the holes and stains the garment of the wearer. Therefore, it is necessary to impart a leakage-preventing property to the entire surface of the back sheet of the diaper.

Further, the underpants type disposable diaper disclosed in the above-mentioned Japanese Unexamined PCT Publication No. 1-503473, Japanese Unexamined Patent Publication No. 4-161,152, Japanese Unexamined Patent Publication No. 5-76,565 and Japanese Unexamined Patent Publication No. 6-63,074, have an outermost layer consisting of a single ply of a nonwoven fabric, or a liquid-absorbent pad member partially adhered to the outermost layer sheet. Therefore, this diaper is disadvantageous in that the outermost layer sheet sometimes is broken or tears, or during wearing, the liquid absorbent pad member is sometimes removed from the outermost layer sheet so that the diaper is deformed.

SUMMARY OF THE INVENTION

An object of the present invention is to provide a disposable diaper having a satisfactory fit to the wearer and moisture-permeability, and capable of fully preventing leaks of liquid from the diaper.

The above-mentioned object can be attained by the disposable diaper of the present invention which comprises:

(A) an outer member having front and back waist sections located at the front and back end portions of the outer member and a pair of crotch sections each having an inwardly indented portion by which a crotch opening is formed when both side edge portions of the front waist section are connected to both side edge portions of the back waist sections; and (B) a liquid absorbent member arranged on a middle portion of the outer member and extending along the longitudinal direction of the diaper, wherein the outer member (A) comprises (a) an outermost sheet layer capable of elongation in the transverse direction of the diaper and (b) a pair of side liner sheet layers covering both the side portions of the outermost sheet layer and extending along the longitudinal direction of the diaper, and the liquid absorbent member (B) comprises (c) a liquid non-permeable back sheet layer located on the middle portion of the outermost sheet layer (a), (d) a liquid permeable top sheet layer superposed on the liquid non-permeable back sheet layer (c), and (e) a liquid absorbent pad layer interposed between the liquid non-permeable back sheet layer (c) and the liquid permeable top sheet layer (d), each of the side liner sheet layers (b) consisting of a composite sheet which comprises (i) an elastic sheet ply capable of expansion and contraction in the transverse direction of the diaper and (ii) at least one non-elastic sheet ply laminated on at least one surface of the elastic sheet ply (i) and capable of elongation in the transverse direction of the diaper.

In an embodiment of the diaper of the present invention, the composite sheet for the side liner sheet layer (b) exhibits an elastic stress of 300 g/25 mm or less under an elongation of 50% in a direction in which the elastic sheet layer is capable of expansion and construction, and a recovery of 80% or more from expansion when the elastic stress is released.

In the composite sheet for the side liner sheet layers (b) of this embodiment, preferably, the elastic sheet ply (i) consists of an elastic, non-porous polyurethane resin film having a moisture-permeability of 2000 to 6000 g/m$^2$·24 hr, and the non-elastic sheet ply (ii) consists of a nonwoven fabric.

DESCRIPTION OF THE PREFERRED EMBODIMENTS

Figure 1:
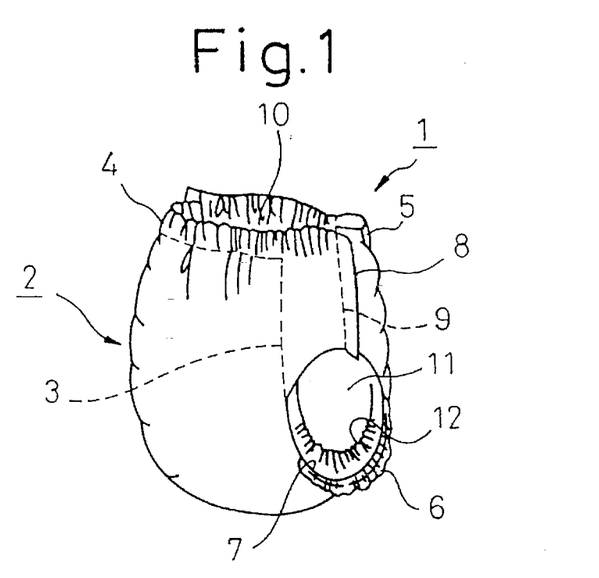
FIG. 1 is a perspective view of an embodiment of the underpants type disposable diaper of the present invention.

An embodiment of the disposable diaper of the present invention is shown in FIG. 1.

In FIG. 1, an underpants type disposable diaper 1 comprises an outer member 2 and a liquid absorbent member 3 arranged on a middle portion of the inside surface of the outer member 2 and extending along the longitudinal direction of the diaper 1. The outer member 2 has a front waist section 4 and a back waist section 5 located at the front and back end portions of the outer member 2 and a pair of crotch sections 6 each having an inwardly indented portion 7. When the side edge portions 8 of the front waist section 4 are joined, for example, by seaming, to side edge portion 9 of the back waist section 5, a waist opening 10 and a pair of crotch openings 11 are formed. The diaper 1 has a pair of flaps 12 extending from the inside surface of the diaper 1.

The front and back waist sections 4 and 5 and the crotch sections 6 are capable of expansion and contraction.

In the disposable diaper of the present invention, the outer member comprises an outermost sheet layer capable of elongation in the transverse direction of the diaper and a pair of side liner sheet layers covering both the side portions of the outermost sheet layer, extending along the longitudinal direction of the diaper. The pair of side liner sheet layers are separated and spaced from each other through the middle portion of the outermost sheet layer.

The liquid absorbent member comprises a liquid non-permeable back sheet layer located on the middle portion of the outer member, a liquid permeable top sheet layer superposed on the liquid non-permeable back sheet layer, and a liquid absorbent pad layer interposed between the liquid non-permeable bottom sheet layer and the liquid permeable top sheet layer.

Figure 2:
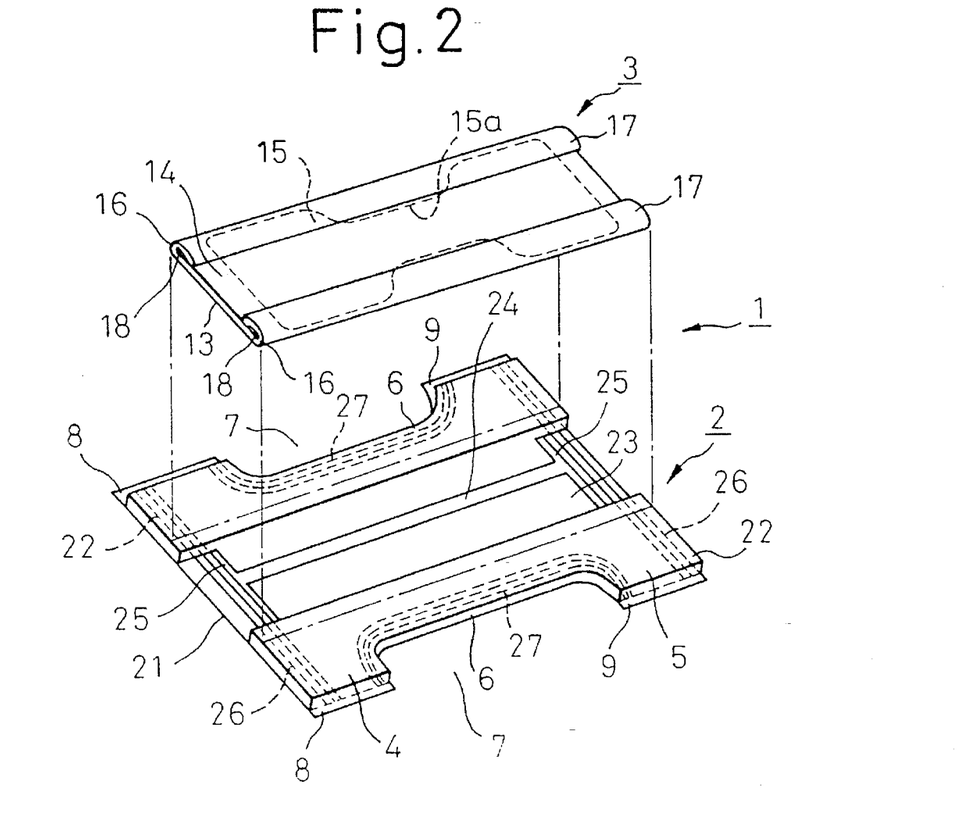
FIG. 2 is an exploded perspective explanatory view of an embodiment of the underpants type disposable diaper of the present invention which has a liquid absorbent member and an outer member and is now opened and flattened.

FIG. 2 is an explanatory exploded view of the disposable diaper of the present invention, when the diaper is opened and flattened. In FIG. 2, the diaper 1 comprises an outer member 2 and a liquid absorbent member 3 which is indicated separately from the outer member 2.

The liquid absorbent member 3 comprises a liquid non-permeable back sheet layer 13, a liquid permeable top sheet layer 14 superposed on the back sheet layer 13 and a liquid absorbent pad 15 interposed between the back sheet layer 13 and the top sheet layer 14. The liquid absorbent pad 15 is in the shape of, for example, a dumbbell as shown by dotted lines 15a in FIG. 2, or in a rectangular form, and has a largest width and largest length which are respectively smaller than the width and length of the top sheet layer 14.

Thus, the liquid absorbent pad 15 does not extend to the outside of the top sheet layer 14.

At the side edges 16 of the liquid absorbent member 3, a pair of flaps 17 is formed from the side edge portions of the liquid non-permeable back sheet layer 13. The side edge portions of the back sheet layer 13 are folded to provide spaces for receiving elastic members 18 which are attached to the flaps 17 and make the flaps 17 capable of expansion and contraction.

When the flaps 17 contract, the flaps 17 rises at the side edge 16, and the liquid absorbent member 3 bends so as to form together with the flaps 17 a bag. In this bag, the flaps 17 serve as gathering side walls.

The elastic members 18 may be attached to the side edge portions of the back sheet layer 13, without folding the side edge portions. Each elastic member 18 may consist of one or two or more elastic threads or tapes.

In the liquid absorbent member, the top sheet layer is formed from a liquid permeable nonwoven fabric comprising a thermoplastic fibers, for example, polyethylene or polypropylene fibers.

Preferably, the nonwoven fabric for the top sheet layer has a thickness of 200 to 500 μm.

The back sheet layer is formed from a liquid non-permeable thermoplastic resin film, for example, polyethylene film or polypropylene film. The liquid non-permeable film is preferably moisture-permeable. Namely, the liquid non-permeable, moisture permeable film has a plurality of very fine holes which allow moisture to pass therethrough but not allow a liquid to pass therethrough. The liquid non-permeable, moisture permeable thermoplastic resin film can be produced by forming an undrawn thermoplastic resin film comprising a thermoplastic resin matrix and a plurality of fine solid filler particles and drawing the undrawn film in at least one direction. This liquid non-permeable, moisture permeable sheet layer effectively prevents the undesirable stuffiness of the wearer of the diaper. The liquid non-permeable sheet layer preferably has a thickness of 20 to 40 μm.

The liquid absorbent pad preferably comprises fluff pulp fibers and a high water-absorbent polymeric material, for example, starch, copolymers of starch with grafted acrylic acid, and polyacrylates. The liquid absorbent pad may be formed from a high liquid absorbent paper sheet alone containing the high water absorbent polymeric material blended with the fluff pulp fibers and optionally heat-fusible synthetic fibers, or a laminate of two or more of the high liquid absorbent paper sheets. Also, the laminate may consist of a lower sheet layer formed from a blend or laminate of the fluff pulp fibers and the high water absorbent polymeric material, a upper sheet layer formed from the fluff pulp fibers, and a packing sheet by which the laminate of the upper and lower sheet layers is wrapped. As mentioned above, the liquid absorbent pad may be in a dumbbell or hourglass shape or a rectangular shape. Usually, the dumbbell shape liquid absorbent pad is preferred to improve the fit of the resultant diaper to the wearer.

The flaps of the liquid absorbent member are preferably formed from side edge portions of the liquid non-permeable sheet layers, extending from the side edges of the liquid absorbent member to the outside thereof. The flaps may be formed from a liquid non-permeable sheet other than that for the liquid non-permeable sheet layer.

The flaps may be formed from a laminate sheet consisting of a liquid non-permeable film having a smaller thickness of 5 to 20 μm and a higher softness than those of the liquid non-permeable film for the back sheet layer and a nonwoven fabric made from synthetic hydrophobic fibers and having a basis weight of 10 to 25 g/m$^2$.

In the laminate sheet for the flaps, the liquid non-permeable film may be laminated on the entire surface of the nonwoven fabric, or on a portion of the surface of the nonwoven fabric. Also, in the laminate sheet for the flaps, the side edges of the liquid non-permeable film may completely meet with the side edges of the nonwoven fabric laminated on the liquid non-permeable film, or the side edge portions of the nonwoven fabric may extend to the outside of the side edges of the liquid non-permeable film. The lamination of the liquid non-permeable film and the nonwoven fabric on each other can be carried out by a conventional laminating method, for example, an extrude-laminating method, dry laminating method, fuse-press-bonding method by a heat-embossing machine, a hot melt bond-laminating method or an ultrasonic bond-laminating method.

The elastic members for the flaps may comprise conventional elastic material for conventional disposable diaper, for example, a polymethane film or tape, polyurethane thread, a polyurethane foam or rubber thread. The elastic member is adhered in an expanded (or stretched) condition thereof to the terminal portions of the flaps through a hot melt adhesive.

In FIG. 2, the outer member 2 comprises an outermost sheet layer 21 and a pair of side liner sheet layers 22 covering both side portions of the outermost sheet layer 21 and extending along the longitudinal direction of the diaper 1.

The outer member 2 (the outermost sheet layer 21 and the side liner sheet layers 22) has a pair of inwardly indented portions 7 to form the crotch openings 11 when the front and back waist sections 4 and 5 of the outer member 2 are joined at the side edge portions thereof to each other.

The outermost sheet layer 21 is formed from a non-elastic sheet, for example, a nonwoven fabric comprising at least one member selected from, for example, polyester fibers, for example, polyethylene terephthalate fibers, polyamide fibers, for example, nylon 66 fibers, cellulose fibers, for example, cotton fibers or wood pulp fibers, and produced by, for example, water jet-entangling the fibers with each other. The nonwoven fabric may be hydrophilic or hydrophobic. The non woven fabric can be elongated under a stretching load, but cannot elastically contract when released from the stretching load.

The liquid absorbent member 3 is placed on the middle portion 23 of the outermost sheet layer 21 and adhered thereto, for example, at a central adhering region 24 extending in the longitudinal direction and a pair of terminal adhering regions 25 extending in the transverse direction of the middle portion 23.

The adhesion of the liquid absorbent member 3 to the middle portion 23 of the outermost sheet layer 21 by using a hot melt adhesive. The adhesive may be applied to the entire surface area of the middle portion 23 of the outermost sheet layer 21. However, to enhance the skin feeling of the resultant diaper for the wearer, it is preferred that the adhesive be applied to specific regions of the middle portion 23 of the outermost sheet layer 21. The adhering regions on the middle portion 23 may be in any form, for example, in the form of a straight line, a broken line, a plurality of dots, a curved line or a spiral line. Preferably, the adhering regions are located in the longitudinal center portion 24 and both the transverse terminal portions 25 of the middle portion 23 and in an H-form. However, the location of the adhering regions is not limited to that in FIG. 2. Another location of the adhering regions will be shown in FIG. 8.

In the disposable diaper of the present invention, each of the side liner sheet layers consists of a composite sheet which comprises an elastic sheet ply capable of expansion and contraction in the transverse direction of the diaper and at least one non-elastic sheet ply laminated on at least one surface of the elastic sheet ply and capable of elongation in the transversal direction of the diaper.

The composite sheet for the side liner sheet layers preferably exhibits an elastic stress of 300 g/25 mm or less under an elongation of 50% in a direction in which the elastic sheet ply is capable of expansion and contraction, and a recovery of 80% or more from the elongation when the elastic stress is released.

Also, in the composite sheet for the side liner sheet layers, the elastic sheet ply preferably consists of an elastic, non-porous polyurethane resin film having a moisture-permeability of 2,000 to 6,000 g/m$^2$·24 hr, and the non-elastic sheet ply preferably consists of a nonwoven fabric.

Further, in an embodiment of the disposable diaper of the present invention, the outermost sheet layer consists of a composite sheet which comprises an elastic sheet layer capable of expansion and contraction in the transverse direction of the diaper and at least one non-elastic sheet layer laminated on at least one surface of the elastic sheet layer and capable of elongation in the transverse direction of the diaper. The composite sheet for the outermost sheet preferable exhibits an elastic stress of 300 g/25 mm or less under an elongation of 50% in a direction in which the elastic sheet layer is capable of expansion and contraction, and a recovery of 80% or more from the elongation when the elastic stress is released.

The elastic sheet may be a moisture permeable elastic polyurethane film or sheet, natural rubber sheet or elastic foamed sheet. In the composite sheet for the outermost sheet, the elastic sheet layer preferably consists of an elastic, non-porous polyurethane resin film having a moisture-permeability of 2,000 to 6,000 g/m$^2$·24 hr, and the non-elastic sheet layer preferably consists of a nonwoven fabric.

The polyurethane resin film usable as an elastic sheet ply of the side liner sheet layers and/or the outermost sheet layer is made from a polyurethane elastomer resin, preferably containing, as a principal component, a polyether type polyurethane elastomer. The polyurethane resin film is elastic and non-porous and preferably exhibits a moisture-permeability of 2,000 to 6,000 g/m$^2$ per 24 hours and a pressure resistance of 9,806.65 Pa or more (1,000 mmH$_2$O/cm$^2$ or more) and has a thickness of 5 to 40 µm, more preferably 10 to 20 µm. The polyurethane resin film is available, for example, under the trademark of SOFRAN-PARM FILM, from TOYO GOMUKOGYO K.K. Also, the polyurethane film may be selected from those disclosed in Japanese Unexamined Patent Publication (Kokai) Nos. 62-292,412 and 62-290,714. Those polyurethane films comprise a polyetherester type polyurethane.

The nonwoven fabric usable as the non-elastic sheet ply for the composite sheet for the side liner sheet layers and the outermost sheet layer is preferably produced by spouting fluid streams, for example, water jet streams against a fiber or filament web to cause the fibers or filaments in the web to be entangled with each other. Also, the nonwoven fabric is air-permeable and liquid (water)-permeable and preferably has a basis weight of 10 to 90 g/m$^2$ more preferably 20 to 40 g/m$^2$. The nonwoven fabric is non-elastic and capable of elongation in the transverse direction of the diaper. The nonwoven fabric is preferably formed from at least one member selected from fibers and filaments of polyesters, for example, polyethylene terephthalate, polyolefins, for example, polyethylene and polypropylene, polyamides, for example, nylon 6 and nylon 66, and cellulose pulp. These fibers or filaments are used alone or in a mixture of two or more thereof. The fibers usable of the nonwoven fabric preferably have a length of 10 to 80 mm, more preferably 38 to 63 mm and a thickness of 1 to 5 d tex, more preferably 2 to 4 d tex. More preferably, the nonwoven fabric is made from a blend of polyethylene terephthalate fibers with hot melt bonding fibers, or core-in-sheath type conjugate fibers in which the sheath portions consist of a hot melt bonding resin.

In an example of the method of producing the nonwoven fabric, a synthetic fiber web is formed on a support by a carding method, and then converted to a nonwoven fabric by spouting water jet streams against the fiber web so as to cause the fibers in the web to be entangled with each other. The water-jet entanglement is preferably carried out by spouting a plurality of water jet streams through water jet nozzles arranged in intervals of 0.5 to 2 mm from each other and having an inside diameter of 0.07 to 2 mm, under a high pressure of 3 to 300 kg/cm$^2$ more preferably 20 to 60 kg/cm$^2$, against the fiber web placed on a support consisting of a 70 to 100 mesh net and moving at a velocity of 30 to 100 m/min.

When the fiber web contains hot melt bonding fibers mixed with high melting temperature fibers or non-fusible fibers, a heat treatment at a temperature at which the hot melt bonding fibers are melted, is applied to the fiber web to bond therethrough the high melting temperature fibers or the non-fusible fibers to each other and to enhance the surface strength of the resultant nonwoven fabric.

In the production of the composite sheet, the elastic sheet is adhered, while it is maintained in a non-expanded condition, to the non-elastic sheet through a hot melt adhesive. Preferably the hot melt adhesive comprises a hot melt synthetic rubber material, for example, styrene-isoprene block copolymers.

The hot melt adhesive usable for the present invention is obtainable under the trademark of DISPO MELT ME-4, from Kanebo N.S.C. K.K.

The hot melt adhesive can be applied by any conventional adhering method, for example, beading method, spiral method or melt blow method. To minimize the influence of the adhesive on the expansion and contraction property of the resultant composite sheet, and obtain a good hand feel of the composite sheet, it is necessary to minimize the amount of the adhesive and evenly distribute the adhesive throughout the adhering surface. For this purpose, the melt blow method is most preferred.

In FIG. 2, a pair of elastic members 26 is attached to the terminal portions of the front and back waist sections 4 and 5 so as to cause the terminal portions of the waist sections 4 and 5 to be capable of expansion and construction in the transverse direction of the diaper. Also, a pair of elastic members 27 is attached to the inwardly indented edge portions of the crotch sections 6 so as to cause the edge portions to be capable of expansion and contraction.

In the disposable diaper of the present invention, a non-elastic intermediate sheet layer may be interposed between the outermost sheet layer and the liquid absorbent member, and connected to the side liner sheet layers.

In an embodiment, the composite sheet for the side liner sheet layers and optionally for the outermost sheet was prepared by the following procedures.

A web was prepared from a blend of polyethylene terephthalate staple fibers having a thickness of 1.56 d tex (1.4 denier) and a length of 51 mm with a core-in-sheath type composite staple fibers each composed of a core consisting of a polyethylene terephthalate and a sheath consisting of a polyethylene, having a thickness of 2.2 d tex (2 denier) and a length of 51 mm, and available under the trademark of SOFIT, from K.K. Kuraray, in a mixing weight ratio of 1:1. The web was subjected to an entangling treatment using water jet streams, to produce a non-woven fabric having a basis weight of 24 g/m$^2$, and an ultimate elongation of 250% in the transverse direction of the nonwoven fabric. In this non-woven fabric, the polyester fibers could be bonded to each other by heating the nonwoven fabric at a temperature, at which the polyethylene sheaths could be hot melted, through the hot melted composite bonding fibers.

A polymethane film having a thickness of 15 μm, a moisture permeability of 5,000 g/m$^2$·24 hr, a water pressure resistance of 1,000 mmH$_2$O/cm$^2$ or more, an elastic stress of 80 g/25 mm under an elongation of 50% and an elastic stress of 100 g/25 mm under an elongation of 100%, and available under the trademark of SOFRAN PARM FILM, from Toyo Gomukogyo K.K., was laminated on and bonded to the nonwoven fabric through an adhesive, to provide a composite sheet. The adhesive comprises a low viscosity synthetic rubber and available under the trademark of DISPOMELT ME-4, from Kanebo N.S.C. K.K. In this bonding, the adhesive was evenly applied in from of a plurality of fine fibers on a surface of the polyurethane film by using a curtain coater, and the nonwoven fabric was superposed on and bonded to the polyurethane film through the adhesive. This composite sheet had a satisfactory hand feeling, a high elasticity (capability of expansion and contraction), a high moisture-permeability. Also, this composite sheet had an elastic stress of 135 g/25 mm under an elongation of 50%, an elastic stress of 200 g/25 mm under an elongation of 100% and a recovery of 85% from the 50% elongation when the elastic stress is released.

This composite sheet is useful for forming the side liner sheet layers and optionally the outermost sheet layer of the disposable diaper of the present invention.

Figure 3:
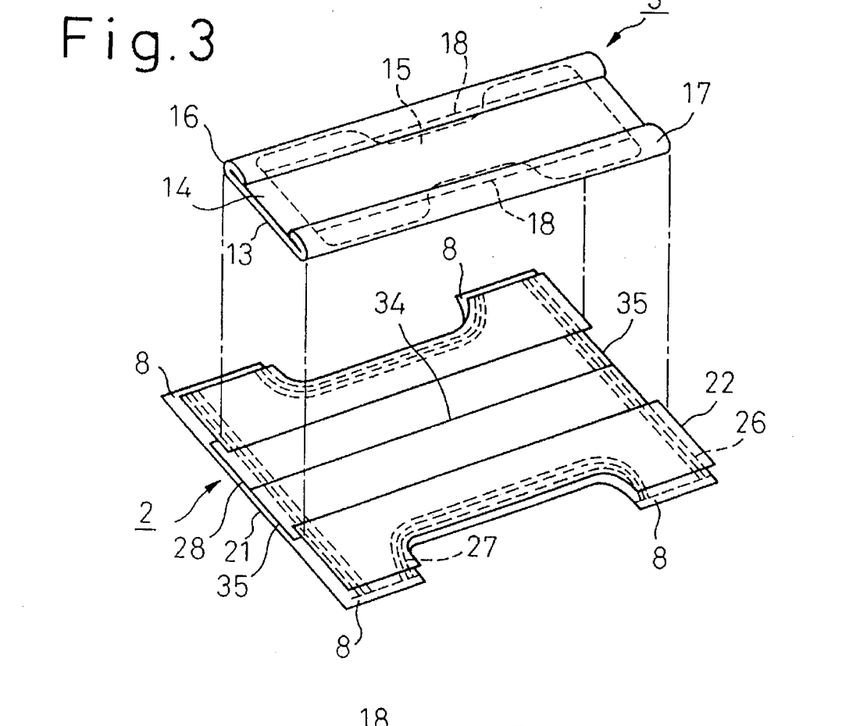
FIG. 3 is an exploded perspective explanatory view of still another embodiment of the underpants type disposable diaper of the present invention now opened and flattened.

The disposable diaper shown in FIG. 3 is the same as that of FIG. 2, except that the middle portion of the outermost sheet layer 21 is reinforced by an non-elastic intermediate sheet layer 28, and on the intermediate sheet layer 28, a central adhering region 34 extending in the longitudinal direction and a pair of terminal adhering regions 35 extending in the transverse direction of the intermediate sheet layer 28 are provided. Those adhering regions 35 and 34 are in an H form.

Figure 4:
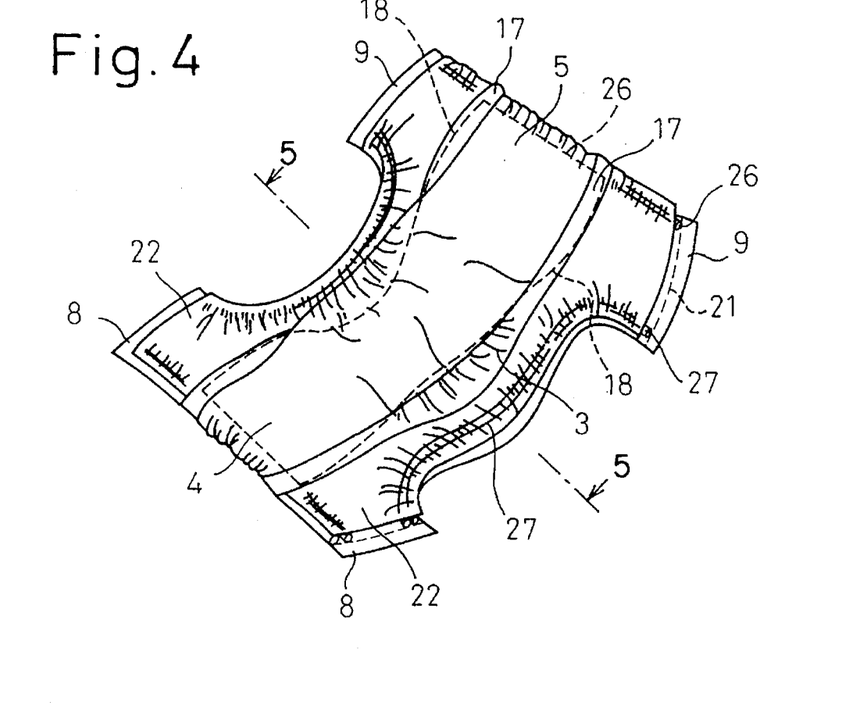
FIG. 4 is a perspective explanatory view of the opened underpants type disposable diaper of FIG. 3.

FIG. 4 shows a perspective explanatory view of the underpants type disposable diaper of FIG. 3, which is now opened by disjoining the side edge 8 of the front waist section 4 from the side edge 9 of the back waist section 5.

Figure 5:
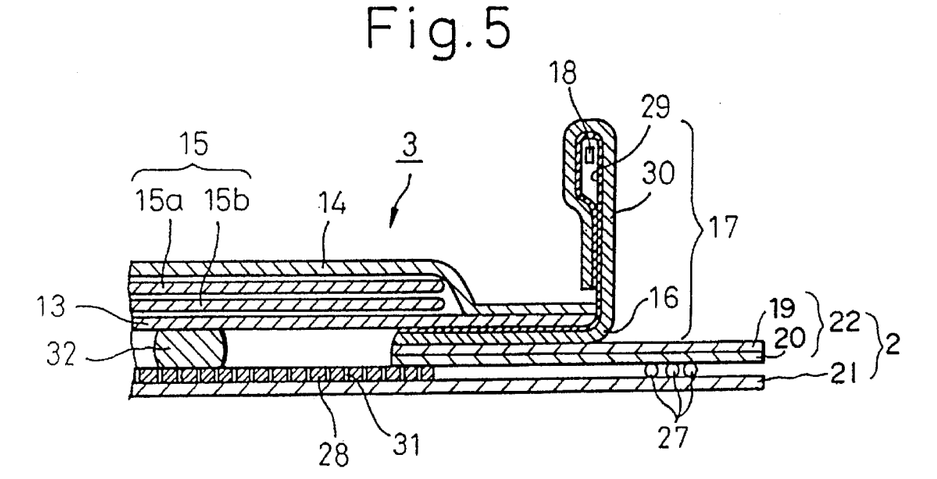
FIG. 5 is an explanatory transverse cross-sectional partial view of the underpants type disposable diaper of FIG. 4, along the line A–A' in FIG. 4.

FIG. 5 shows a portion of a transverse cross-section of the underpants type disposable diaper of FIG. 4, along the line A-A' in FIG. 3.

In FIG. 5, a middle portion of the outermost sheet layer 21 is reinforced by a non-elastic intermediate sheet 28, and side portion of the outermost sheet layer 21 is covered by a side liner sheet layer 22. The side liner sheet layer 22 consists of a composite sheet which comprises an elastic sheet ply 20 capable of expansion and contraction in the transverse direction of the diaper and a non-elastic sheet ply 19 laminated on the upper surface of the elastic sheet ply 20 and capable of elongation in the transverse direction of the diaper. An elastic member 27 consisting of, for example, three rubber threads, as indicated in FIG. 5 is located between the outermost sheet layer 21 and the side liner sheet layer 22. An inside edge portion of the side liner sheet layer 22 overlaps with and adheres to an outside edge portion of the intermediate sheet layer 28. A liquid absorbent member 3 is arranged on the middle portion of the outermost sheet layer 21 through the intermediate sheet layer 28.

The non-elastic intermediate sheet layer may be formed from, for example, a polyethylene porous sheet or film, or a moisture permeable thermoplastic resin film produced by forming an undrawn film from a mixture of a thermoplastic resin and a filler and drawing the film so as to form a plurality of air-permeable pores therein.

In FIG. 5, the flap 17 is located inside of the elastic member 27 arranged in the crotch section 6. The flap 17 comprises a laminate sheet consisting of a liquid non-permeable sheet 29, for example, polypropylene or polyethylene sheet, a nonwoven fabric 30, for example, polyethylene terephthalate or polypropylene fiber nonwoven fabric, and an elastic member 18. The nonwoven fabric 30 is laminated on the liquid non-permeable sheet 29 so as to form an outside face of the flap 17 and the laminate is folded at a top end of the flap and forms a space at the top portion of the flap 17. In this space, the elastic member 18 is contained so as to elasticize the flap 17. This type of flap has a good touch feeling, satisfactory softness and a good fit to the wearer. The lower end portion of the laminate is inserted and fixed between the liquid absorbent member 3 and the side liner sheet 22.

The liquid absorbent member 3 as shown in FIG. 5 has a liquid non-permeable back sheet layer 13, a liquid permeable top sheet layer 14 and a liquid absorbent pad layer 15 consisting of two liquid absorbent pads 15a and 15b and packed between the liquid non-permeable back sheet layer 13 and the liquid permeable top sheet layer 14.

In FIG. 5, the intermediate sheet 28 has a plurality of fine holes 31 which cause the intermediate sheet 28 to be moisture and air permeable and are effectively prevent a bad stuffy feeling of the wearer.

The elastic member 27 located in the crotch section 6 causes the crotch section 6 to fully fit at a certain area thereof to the crotch of the wearer and to effectively minimize leaking of a liquid from the crotch section 6.

As shown in FIG. 5, the outside edge portion of the intermediate sheet layer 28 is adhered to the inside edge portion of the side liner sheet layer 22. Also, the middle portion of the liquid absorbent member 3 is adhered to the intermediate sheet layer 28 through an adhesive layer 32. The adhesive layer 32 preferably has a width of 1 to 20 mm.

In the disposable diaper as shown in FIGS. 1 to 5, the side liner sheet layer 22 is formed from a specific composite sheet of the present invention and elasticized by the elastic member 27, and thus even when the wearer of the diaper lies on one's side, leaking of a liquid from the crotch section 6 can be fully prevented. Also, the composite sheet has a satisfactory air and moisture permeability and thus the wearer is not subjected to a stuffy feeling even if the liquid non-permeable back sheet layer 13 of the liquid absorbent member 3 is moisture-non-permeable.

In the disposable diaper of the present invention, not only the side liner sheet, but also the outermost sheet layer may consist of the composite sheet as defined hereinbefore. This composite sheet for the outermost sheet may be the same as or different from the composite sheet for the side liner sheet.

Figure 6:
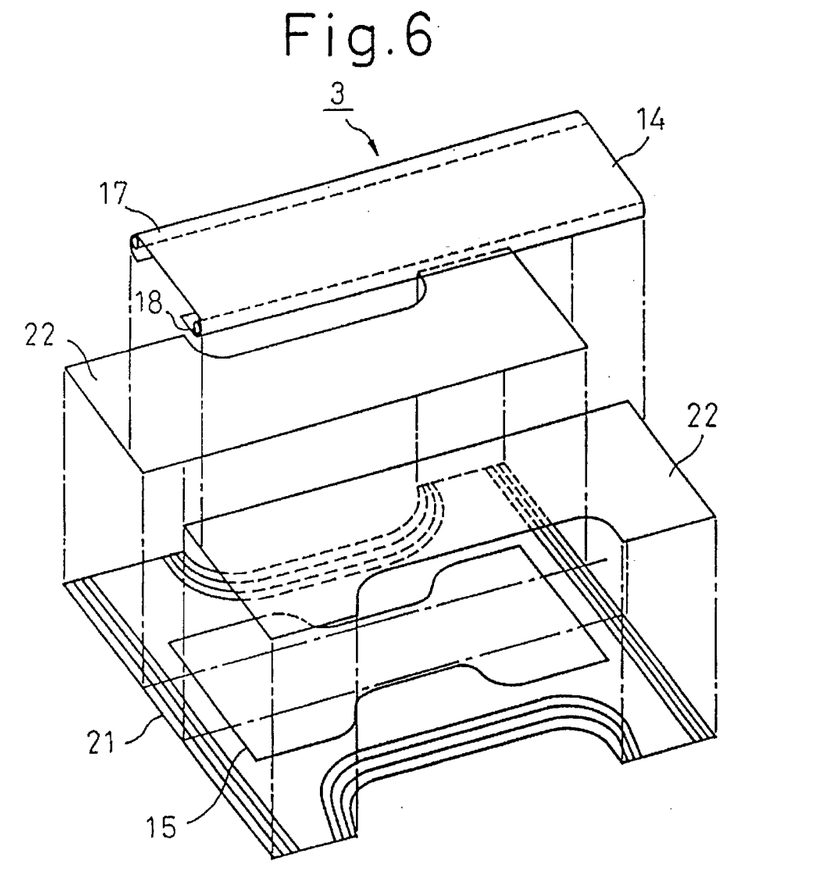
FIG. 6 is an exploded perspective explanatory view of another embodiment of the underpants type disposable diaper of the present invention now opened and flattened.

FIG. 6 shows an exploded perspective explanatory view of an embodiment of the disposable diaper of the present invention now opened and flattened, in which diaper, the outermost sheet consists of the composite sheet.

The composite sheet for the outermost sheet consists of an elastic sheet ply capable of expansion and construction in the transverse direction of the diaper and at least one non-elastic sheet ply laminated on at least one surface of the elastic sheet ply and capable of elongation in the transverse direction of the diaper. The elastic sheet ply is non-porous and liquid non-permeable, and serves as a liquid non-permeable back sheet layer of the liquid absorbent member.

The composite sheet for the outermost sheet layer preferably exhibits an elastic stress of 300 g/25 mm or less under an elongation of 50% in a direction in which the elastic sheet ply is capable of expansion and contraction and a recovery of 80% or more from expansion when the elastic stress is released.

In the composite sheet for the outermost sheet layer, the elastic sheet ply preferably consists of an elastic, non-porous (liquid non-permeable) polyurethane resin film having a moisture-permeability of 2000 to 6000 g/m$^2$·24 hr, and the non-elastic sheet ply consists of a non-woven fabric.

The nonwoven fabric for the non-elastic sheet ply is preferably produced by forming a web from a plurality of fibers or filaments and spouting fluid streams against the web under high pressure so as to entangle the fibers or filaments with each other.

In the preparation of the composite sheet, the elastic sheet, for example, the elastic polyurethane film, is adhered to the non-elastic sheet, for example, the nonwoven fabric, through a hot melt adhesive while the elastic sheet is maintained in a non-expanded condition.

Figure 7:
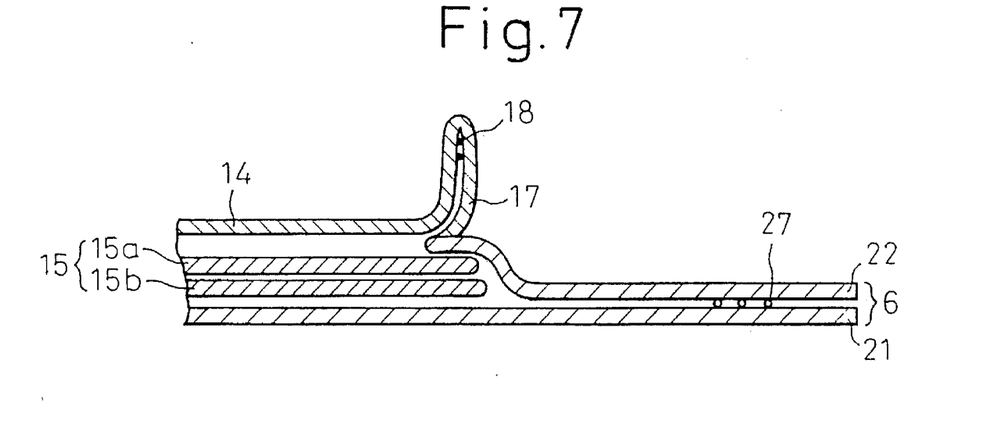
FIG. 7 is an explanatory transverse cross-sectional partial view of the underpants type disposable diaper of FIG. 6.

In FIGS. 6 and 7, a liquid absorbent pad layer 15 is directly arranged on a middle portion of an outermost sheet layer 21 and covered by a liquid permeable top sheet layer 14, to form a liquid absorbent member. A flap 17 is formed from the same liquid permeable sheet as that for the top sheet 14. A side liner sheet layer 22 is formed from a non-elastic nonwoven fabric capable of expansion in the transverse direction of the diaper. The inside edge portion of the side liner sheet layer 22 is inserted between the liquid absorbent pad layer 15 and the top sheet 14 so as to cover the outside edge portions of the liquid absorbent pads 15$a$ and 15$b$. In the flap 17, an elastic member 18 is attached so as to elasticize the flap 17.

Figure 8:
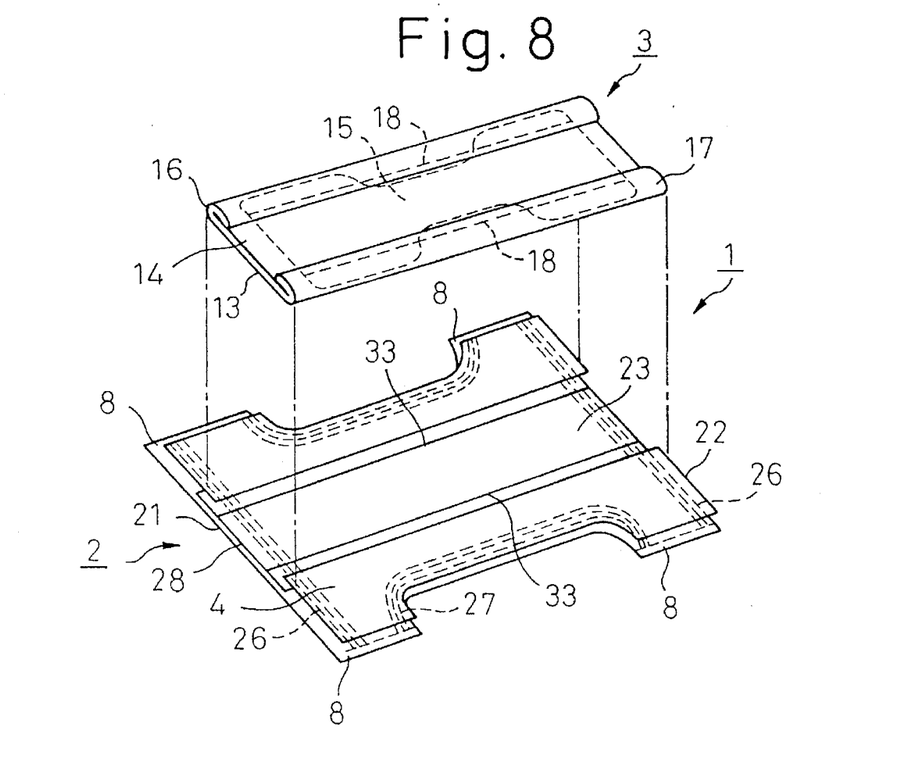
FIG. 8 is an exploded perspective explanatory view of still another embodiment of the underpants type disposable diaper of the present invention now opened and flattened.

In the disposable diaper as shown in FIG. 8, an intermediate sheet layer 28 is placed on a middle portion 23 of an outermost sheet layer 21 and a pair of side liner sheet layers 22 are arranged on a pair of side portions of the outermost sheet layer 21 in such a manner that the inside edge portions of the side liner sheet layer 22 overlap with both the outside edge portions of the intermediate sheet layer 28, and these edge portions are adhered to each other.

A liquid absorbent member 3 is superposed on the intermediate sheet layer 28 and fixed thereto at a pair of adhering regions 33 by an adhesive.

Figure 9:
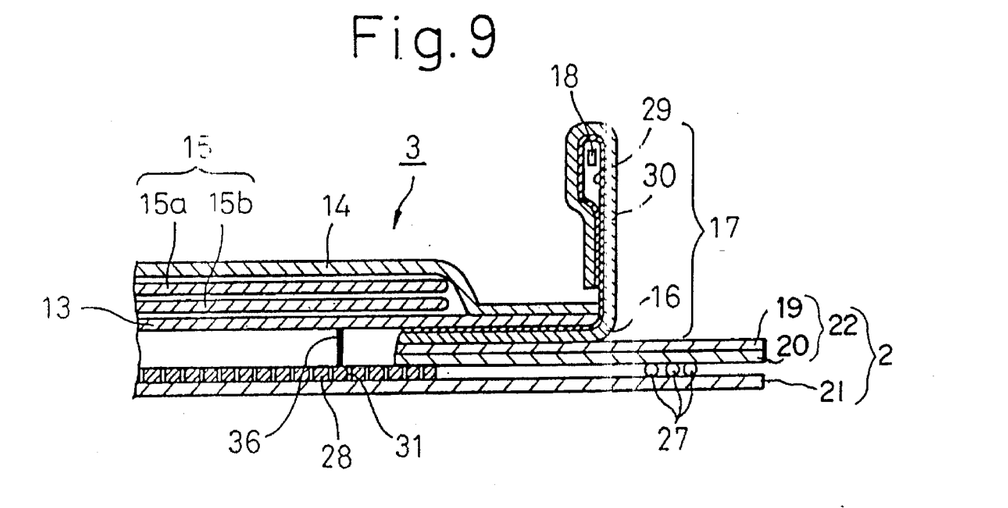
FIG. 9 is an explanatory transverse cross-sectional partial view of the underpants type disposable diaper of FIG. 8.

The constitution of the disposable diaper shown in FIG. 9 is the same as that of FIG. 5, except that the liquid absorbent member 3 is adhered to the intermediate sheet layer 28 at an adhering region 36 located in the outside edge portion of the intermediate sheet layer 28.

Figure 10:
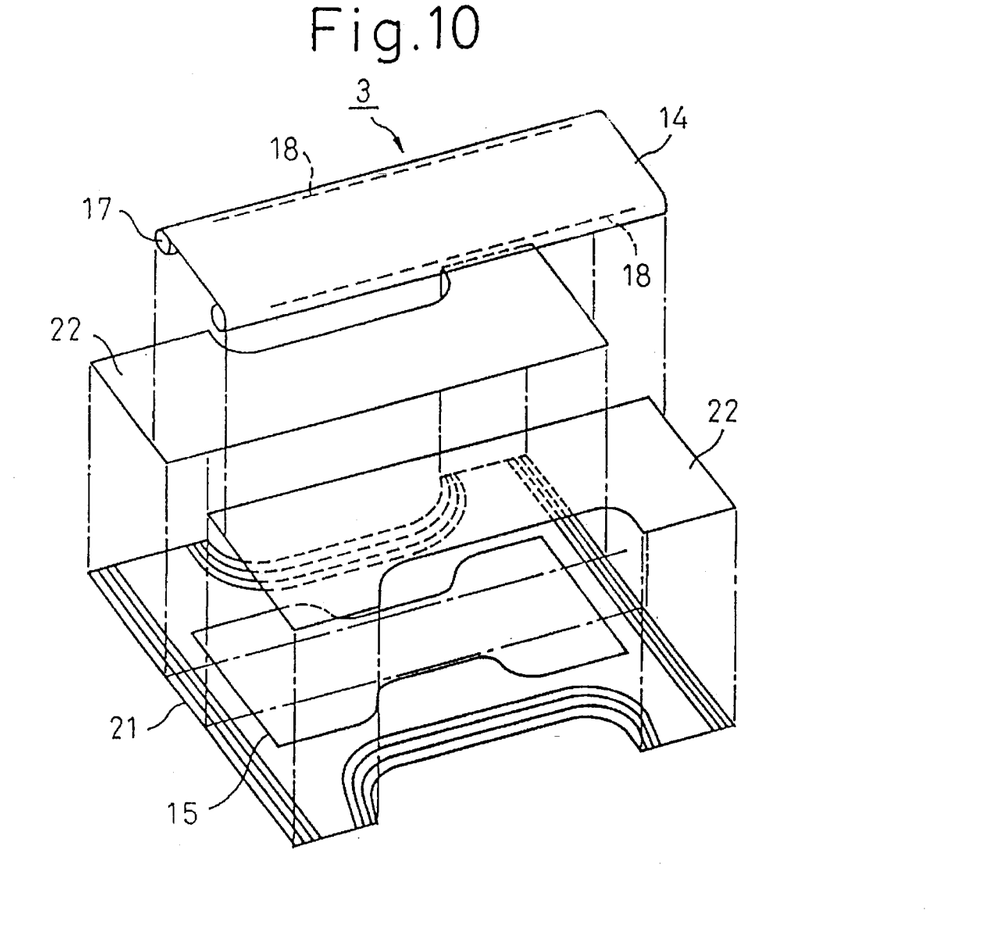
FIG. 10 is an exploded perspective explanatory view of still another embodiment of the underpants type disposable diaper of the present invention now opened and flattened.

The disposable diaper shown in FIG. 10 is the same as that of FIG. 6, except that in the liquid absorbent member 3, a pair of elastic members 18 is located in the middle portions of the flaps 17.

Figure 11:
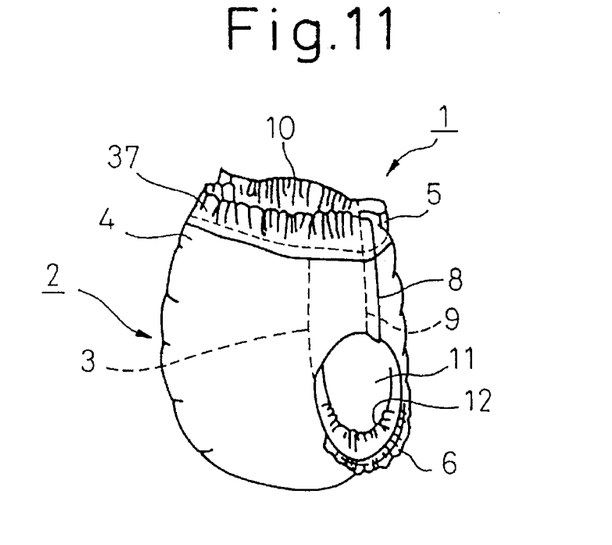
FIG. 11 is a perspective view of still another embodiment of the underpants type disposable diaper of the present invention, which has elastic ribbon members attached to the front and back moist sections.
Figure 12:
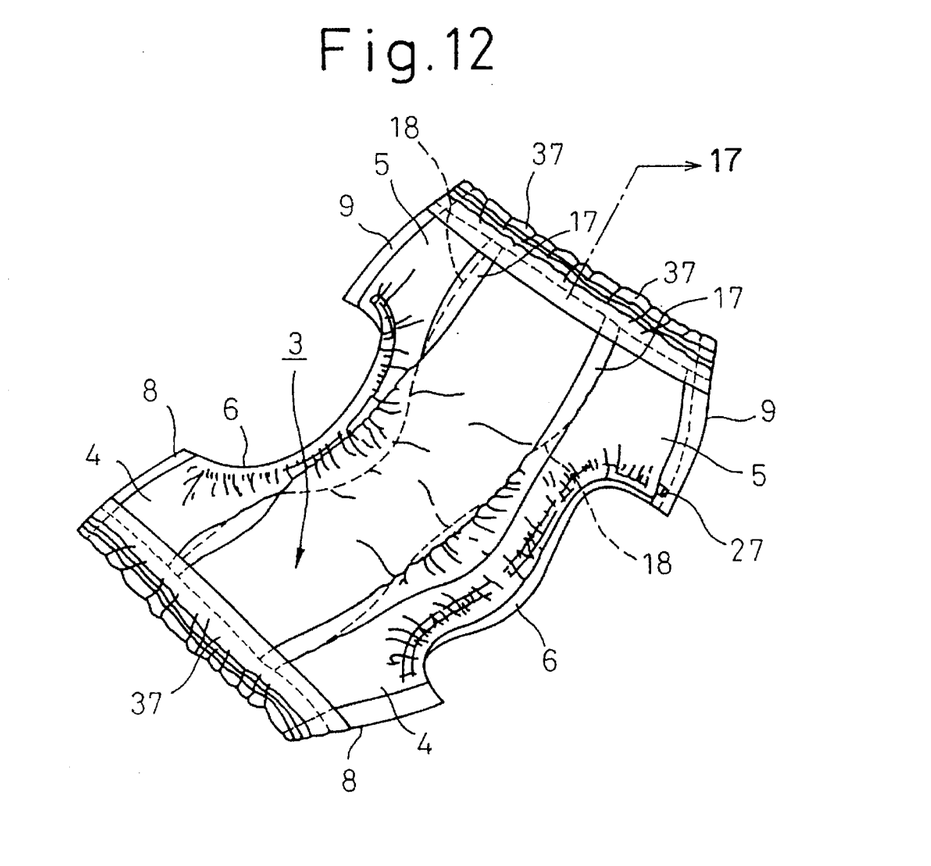
FIG. 12 is a perspective view of the underpants type disposable diaper of FIG. 11 now opened and flattened.

The disposable diaper shown in FIGS. 11 and 12 is the same as that of FIGS. 1, and 4, except that a pair of elastic ribbon members 37 is attached to the outer end portions of the front and back waist sections 4 and 5 of the outer member 2, so as to extend outside of the front and back waist sections 4 and 5, in the longitudinal direction of the diaper and surround the waist opening 10 formed by joining the side edge portions of the front waist section 4 to the side edge portions of the back waist portion 5.

Figure 13:
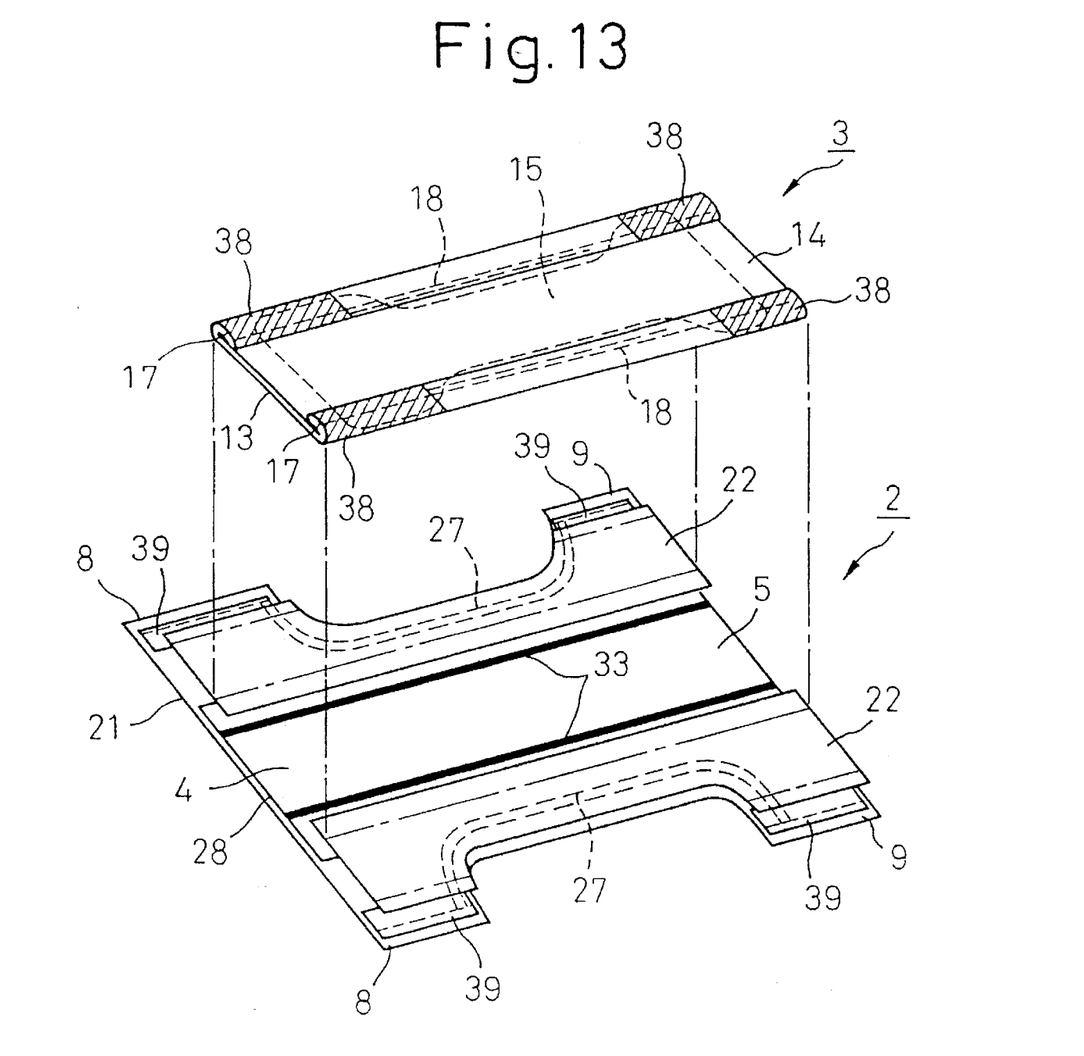
FIG. 13 is an exploded perspective explanatory view of the underpants type disposable diaper of FIG. 11 now opened and flattened.

The disposable diaper shown in FIG. 13 is the same as that of FIG. 8, except that the liquid absorbent member 3 is composed of a liquid non-permeable back sheet layer 13, a liquid permeable top sheet layer 14, superposed on the back sheet layer 13, a liquid absorbent pad layer 15 interposed between the top and back sheet layer 13 and 14, a pair of flaps 17 extending from the side edges of the liquid absorbent member 3 and having elastic members 18 attached to the flaps 17, the side edge portions of the top sheet layer 14 and the back sheet layer 13 and the elastic members 18 are adhered and fixed to each other in the side edge adhering regions 38, by an adhesive (not shown in FIG. 13). When the elastic members 18 are released from elastic stress, it causes the flaps 17 to be elasticized and form gathers as shown in FIG. 12.

The flaps 17 may be formed from side edge portions of the back sheet layer 13 or the top sheet layer 14 or from another sheet material.

In the outer member 2 of FIG. 13, the outermost sheet layer 21 may have four sealing tape members 39 adhered to the side edge portions 8 and 9 of the front and back waist sections 4 and 5. The side edge portions 8 of the front waist section 4 can be joined to the side edge portions 9 of the back waist section 5 through the sealing tape members 39.

Figure 14:
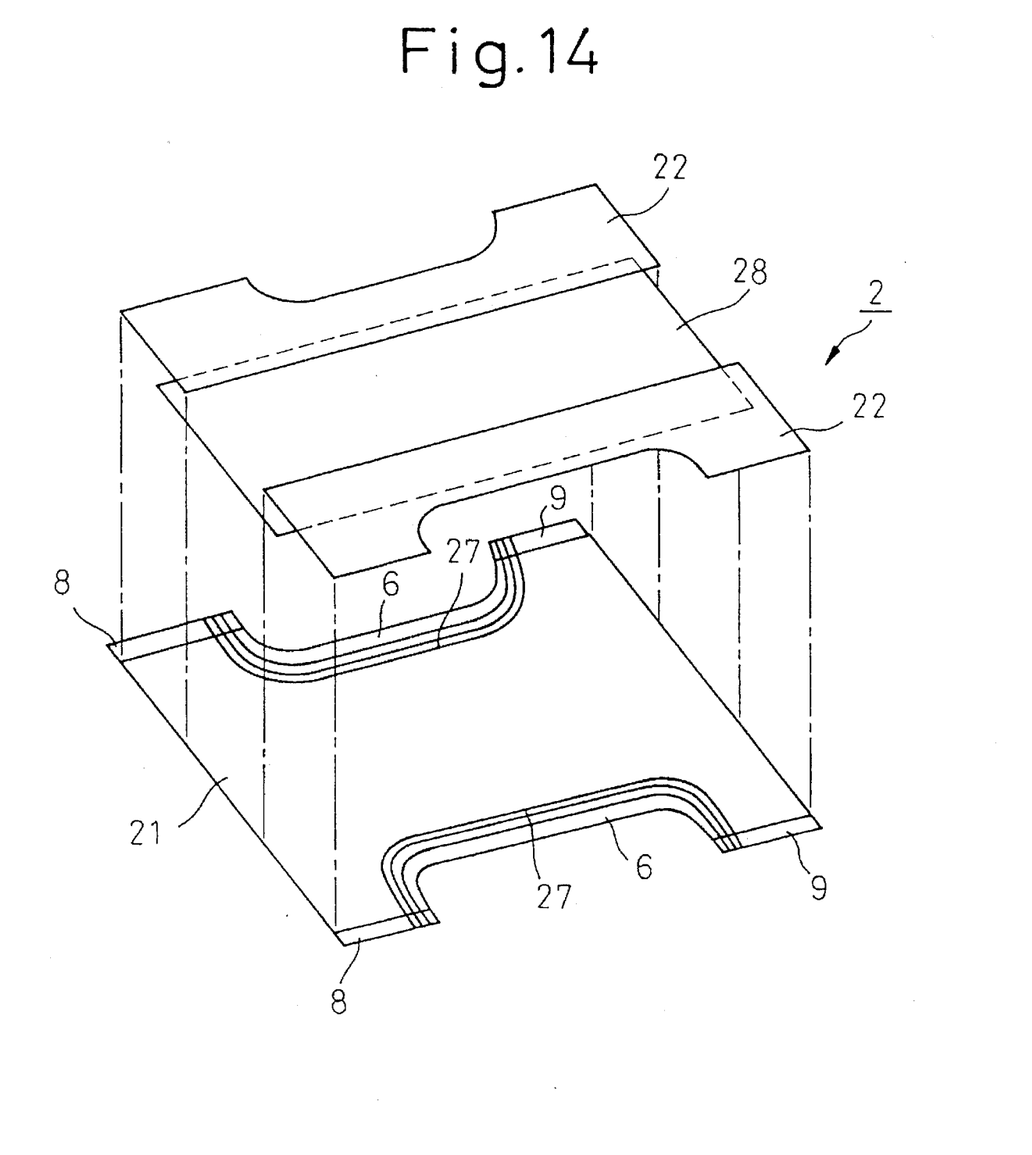
FIG. 14 is an exploded perspective explanatory view of an outer member of underpants type disposable diaper of FIG. 11 now opened and flattened.

FIG. 14 shows an exploded perspective explanatory view of an embodiment of the outer member of the underpants type disposable diaper of FIG. 13.

In FIG. 14, the intermediate sheet layer 28 is placed on a middle portion of the outermost sheet layer 21 and a pair of side liner sheet layers 22 is placed on side portions of the outermost sheet layer 21, and inside edge portions of the side liner sheet layers 22 are overlapped on and adhered to the outside edge portions of the intermediate sheet layer 28. Between the outermost sheet layer 21 and side liner sheet layers 22 and in the inwardly indented crotch sections 6, a pair of elastic members 27 are attached so as to elasticize the crotch sections 27.

Figure 15:
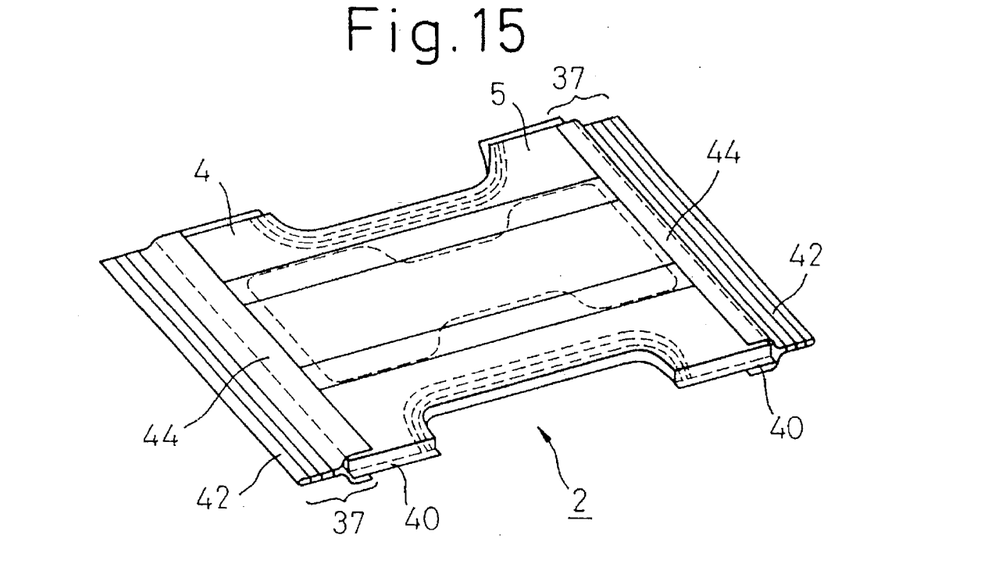
FIG. 15 is a perspective explanatory view of the underpants type disposable diaper of FIG. 11 having elastic ribbon members and now opened and flattened.

In FIG. 15 showing a perspective explanatory view of another embodiment of the disposable diaper of the present invention having a pair of elastic ribbon members and now opened and flattened, a pair of elastic ribbon members 37 are attached to the outer end portions 40 of the outer member 2 so as to cover the outer end portions 40.

Figure 16:
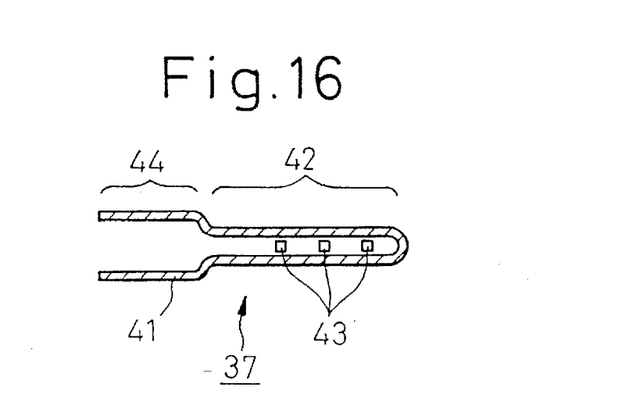
FIG. 16 is a cross-sectional explanatory view of the elastic ribbon member shown in FIG. 15 in a longitudinal direction of the diaper.

As shown in FIG. 16, the elastic ribbon member 37 is formed from a sheet 41 which is folded at a center portion thereof to form a waist flap 42 consisting of the folded two plies facing each other. In the waist flap 42, an elastic member 43 consisting of, for example, three elastic threads is contained between the facing two plies and fixed therein. In another end portion 44 of the elastic ribbon member 37, two end portions of the sheet 41 are free from each other and face each other. The facing end portion 44 forms a grasping belt portion of the elastic ribbon member 37.

In the grasping belt portion 44, an outer end portion 40 of the front or back waist section 4 or 5 is inserted between the two facing end portions of the folded sheet 41 and fixed thereto.

Figure 17:
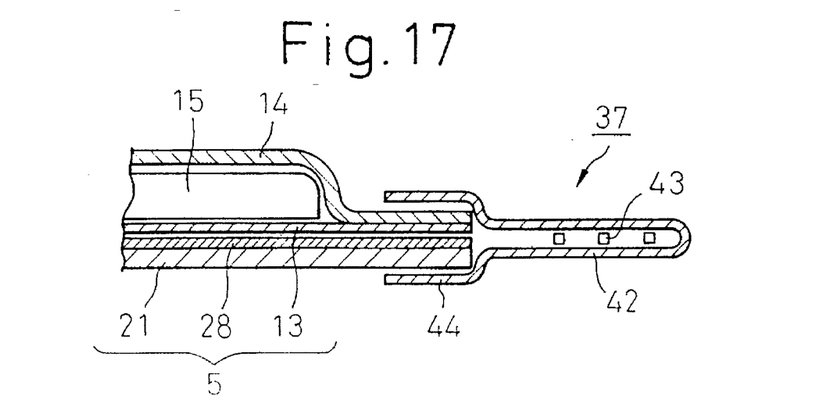
FIG. 17 is a cross-sectional explanatory view of the elastic ribbon member attached to a longitudinal end portion of the underpants type disposable diaper of FIG. 15, along a line A of FIG. 12.

In FIG. 17, an outer end portion of the back waist section 5 is inserted into and fixed to the grasping belt portion 44 of the elastic ribbon member 37.

When the wearer, particularly a child wears the underpants type diaper by himself, it is important that the diaper can be easily worn and taken off. Also, to enhance the appearance of the wearer and to prevent slipping down of the diaper, it is necessary that the diaper closely fit to the waist and hip of the wearer. For this purpose, the elastic ribbon members are attached to the outer end portions of the front and back waist sections, while maintaining both the elastic ribbon members and the outer end portions of the front and back waist sections under tensioned conditions in the transversal direction of the diaper. When the front and back waist sections are released from tension, the waist flap portions of the elastic ribbon members are elasticized so as to enhance the freedom of the front and back waist sections from expansion and contraction, and form gathers in the ribbon members. Also, the waist opening of the underpants type diaper can be easily enlarged and thus the diaper can be easily worn or taken off by the wearer.

Optionally, other elastic members are attached to the grasping belt portions of the elastic ribbon members, in addition to the elastic members attached to the waist flap portions thereof.

The elastic members for the waist flap portions and optionally for the grasping belt portions are fixed thereto by an adhesive, for example, a hot melt adhesive.

The sheet for the elastic ribbon members is preferably selected from nonwoven fabrics of thermoplastic fibers, for example, polyethylene fibers, polypropylene fibers and polyester fibers. To enhance the fit of the waist sections to the wearer, the nonwoven fabric preferably has a high bulkiness and softness. The waist flap portions of the elastic ribbon members preferably have a width of 5 to 50 mm, more preferably 20 to 30 mm. If the width is less than 5 mm, the elastic pressure of the waist sections may be applied locally to the wearer and a pressed mark is formed on the waist. If the width is more than 50 mm, sometimes, the appearance of the resultant diaper becomes unsatisfactory and the resultant elastic ribbon members are easily folded inwardly during wearing. Also, the grasping belt portions preferably have a width large enough to firmly adhere the grasping belt portions the waist sections, preferably 5 to 20 mm when they are adhered to each other by a hot melt adhesive.

In the disposable diaper of the present invention, it is preferable to fix the side edges of the front waist section to the side edge of the back waist section so as to form an underpants type diaper, by means of an adhesive or seam. However, the side edges of the front waist section may be repeatedly fastened and removed from the side edges of the back waist section by using fasteners.

In the disposable diaper of the present invention, since the side liner sheet layers are formed from a specific composite sheet, the resultant diaper has a satisfactory fit to the wearer, an excellent moisture permeability and a good touch feeling and can prevent an undesirable leaking of liquid and a stuffy feeling.

We claim:

1. A disposable diaper comprising:

(A) an outer member having front and back waist sections located at the front and back end portions of the outer member and a pair of crotch sections each having an inwardly indented portion by which a crotch opening is formed when side edge portions of the front waist section are connected to side edge portions of the back waist sections, and comprising (a) an outermost sheet layer capable of elongation in a transverse direction of the diaper and (b) a pair of side liner sheet layers covering both side portions of the outermost sheet layer and extending along a longitudinal direction of the diaper; and (B) a liquid absorbent member arranged on a middle portion of the outer member, extending along the longitudinal direction of the diaper, and comprising (c) a liquid non-permeable back sheet layer located on a middle portion of the outermost sheet layer (a), (d) a liquid permeable top sheet layer superposed on the liquid non-permeable back sheet layer (c), and (e) a liquid absorbent pad layer interposed between the liquid non-permeable back sheet layer (c) and the liquid permeable top sheet layer (d), wherein each of the side liner sheet layers (b) consists of a composite sheet which consists of (i) an elastic sheet ply capable of expansion and contraction in the transverse direction of the diaper and (ii) at least one non-elastic sheet ply laminated on at least one surface of the elastic sheet ply (i) and capable of elongation in the transverse direction of the diaper, the composite sheet for the side liner sheet layers (b) exhibits an elastic stress of 300 g/25 mm or less under an elongation of 50% in a direction in which the elastic sheet ply is capable of expansion and contraction, and a recovery of 80% or more from the elongation when the elastic stress is released, the elastic sheet ply (i) of the composite sheet consists of an elastic, non-porous polyurethane resin film having a moisture-permeability of 2000 to 6000 $g/m^2 \cdot 24$ hr, and the non-elastic sheet ply (ii) consists of a nonwoven fabric, and a non-elastic intermediate sheet layer is interposed between a middle portion of the outermost sheet layer (a) and the liquid absorbent member (B) and connected to the side liner sheet layers (b).

2. The disposable diaper as claimed in claim 1, wherein the elastic sheet ply (i) of the composite sheet for the side liner sheet layers (b) is adhered to the non-elastic sheet ply (ii) through a hot melt adhesive while the elastic sheet is maintained in a non-expanded condition.

3. The disposable diaper as claimed in claim 1, wherein the outermost sheet layer (a) consists of a composite sheet which consists of (i) an elastic sheet ply capable of expansion and contraction in the transverse direction of the diaper and (ii) at least one non-elastic sheet ply laminated on at least one surface of the elastic sheet ply (i) and capable of elongation in the transverse direction of the diaper.

4. The disposable diaper as claimed in claim 3, wherein the composite sheet for the outermost sheet layer (a) exhibits an elastic stress of 300 g/25 mm or less under an elongation of 50% in a direction in which the elastic sheet ply (i) is capable of expansion and contraction, and a recovery of 80% or more from expansion when the elastic stress is released.

5. The disposable diaper as claimed in claim 3, wherein the elastic sheet ply (i) of the composite sheet for the outermost sheet layer (a), consists of an elastic, non-porous polyurethane resin film having a moisture-permeability of 2000 to 600 $g/m^2 \cdot 24$ hr, and the non-elastic sheet ply (ii) consists of a nonwoven fabric.

6. The disposable diaper as claimed in claim 5, wherein the elastic sheet of the composite sheet for the outermost sheet layer (a), is adhered to the non-elastic sheet through a hot melt adhesive while the elastic sheet is maintained in a non-expanded condition.

7. The disposable diaper as claimed in claim 1, wherein each of the front and back waist sections of the outer member (A) has an elastic member by which the front and back waist sections are elasticized.

8. The disposable diaper as claimed in claim 1, wherein each of the pair of crotch sections has an elastic member by which each crotch section is elasticized.

9. The disposable diaper as claimed in claim 1, wherein the front and back waist sections are connected in side edge portions thereof to each other.

10. The disposable diaper as claimed in claim 1, wherein a pair of liquid-non-permeable flaps are attached to both side edge portions of the liquid absorbent section and extend substantially along a longitudinal axis of the diaper.

11. The disposable diaper as claimed in claim 1, wherein a pair of elastic ribbon members are attached to the outer end portions of the front and back waist sections of the outer member.

12. The disposable diaper as claimed in claim 11, wherein each elastic ribbon member comprises a waist flap portion having an elastic member by which the waist flap portion is elasticized, and a pair of grasping belt portions extending from the waist flap portion and facing each other, between which one of the outer end portions of the front and back waist sections is interposed and fixed.

* * * * *